United States Patent [19]

Kharitonov et al.

[11] Patent Number: 5,672,777
[45] Date of Patent: Sep. 30, 1997

[54] CATALYSTS FOR PRODUCTION OF PHENOL AND ITS DERIVATIVES

[75] Inventors: Alexander Sergeevich Kharitonov; Gennady Ivanovich Panov; Galina Anatolievna Sheveleva; Larisa Vladimirovna Pirutko; Tatyana Pavlovna Voskresenskaya; Vladimir Ivanovich Sobolev, all of Novosibirsk, Russian Federation

[73] Assignee: Monsanto Company, St. Louis, Mo.

[21] Appl. No.: 608,541

[22] Filed: Feb. 28, 1996

Related U.S. Application Data

[62] Division of Ser. No. 419,361, Apr. 10, 1995, abandoned.
[51] Int. Cl.$^6$ .................................................. C07C 37/60
[52] U.S. Cl. ........................... 568/800; 568/771; 568/754
[58] Field of Search ............................................. 568/800

[56] References Cited

U.S. PATENT DOCUMENTS

| | | |
|---|---|---|
| 4,559,314 | 12/1985 | Shihabi. |
| 4,982,013 | 1/1991 | Gubelmann et al.. |
| 5,001,280 | 3/1991 | Gubelmann et al.. |
| 5,055,623 | 10/1991 | Gubelmann et al.. |
| 5,077,026 | 12/1991 | Nair et al.. |
| 5,098,687 | 3/1992 | Skeels et al.. |
| 5,110,995 | 5/1992 | Kharitonov et al.. |
| 5,367,099 | 11/1994 | Beck et al.. |

FOREIGN PATENT DOCUMENTS

| | | |
|---|---|---|
| 6-9464 | 1/1994 | Japan. |
| 2010790 | 4/1994 | Russian Federation. |
| 2116974 | 10/1983 | United Kingdom. |
| PCT/RU95/00065 | 4/1995 | WIPO. |
| PCT/RU95/00066 | 4/1995 | WIPO. |

OTHER PUBLICATIONS

Panov et al. (1990), The Role of Iron In $N_2$) Decomposition on ZSM-5 Zeolite and Reactivity of the Surface Oxygen Formed, *Journal of Molecular Catalysis*, 61:85–97.

Iwamoto et al. (1983), Catalytic Oxidation by Oxide Radical Ions 1. One–Step Hydroxylation of Benzene to Phenol over Group 5 and 6 Oxides Supported on Silica Gel, *Journal of Physical Chemistry* 87:903–5.

Ono et al. (1988), Functionalization of Benzene By Its Reaction With Nitrogen Oxides Over Solid–Acid Catalysts, *Hetrogeneous Catalysis and Fine Chemicals*:75–82.

Suzuki et al. (1988), Hydroxylation of Benzene with Dinitrogen Monoxide Over H–ZSM–5 Zeolite, *Chemistry Letters–Japan*:953–6.

Burch et al. (1992), Direct Partial Oxidation of Benzene to Phenol on Zeolite Catalyst, *Applied Catalysis A: General* 86:139–46.

Burch et al. (1993), Investigation of Zeolite Catalysts for the Direct Partial Oxidation of Benzene to Phenol, *Applied Catalysis A: General* 103:135–62.

Burch et al. (1993), Factors Affecting the Deactivation of Various Zeolites Used as Catalysts for the Direct Partial Oxidation of Benzene to Phenol, *Applied Catalysis A: General* 106:167–83.

Panov et al. (1992), Oxidation of Benzene to Phenol by Nitrous Oxide Over Fe–ZSM–5 Zeolites, *Applied Catalysis A: General* 82:31–6.

Panov et al. (1993), Oxidative Hydroxylation Using Dinitrogen Monoxide: A Possible Route for Organic Synthesis Over Zeolites, *Applied Catalysis A: General* 98:1–20.

Kharitonov et al. (1993), Ferrisilicate Analogs of ZSM–5 Zeolite as Catalysts for One–Step Oxidation of Benzene to Phenol, *Applied Catalysis A: General* 98:33–43.

Sobolev et al. (1993), Stoichiometric Reaction of Benzene with α–Form of Oxygen on FeZSM–5 Zeolites. Mechanism of Aromatics Hydroxylation by $N_2O$., *Journal of Molecular Catalysis* 84: 117–24.

Zholobenko et al. (1993), Preparation of Phenol Over Dehydroxylated HZSM–5 Zeolites, *Mendeleev Commun.*:28–9.

Sobolev et al. (1993), Catalytic Properties of ZSM–5 Zeolites in $N_2O$ Decomposition: The Role of Iron, *Journal of Catalysis* 139:435–43.

Zholobenko, *Mendeleev Commun*, (1993), pp. 28–29.

*Primary Examiner*—C. Warren Ivy
*Assistant Examiner*—Sreeni Padmanabhan
*Attorney, Agent, or Firm*—Howell & Haferkamp, L.C.

[57] ABSTRACT

Zeolite catalysts useful for the production of phenol and its derivatives by oxidative hydroxylation of benzene and its derivatives by nitrous oxide, e.g. at temperatures of 225°–450° C., having substantially enhanced process characteristics resulting from hydrothermal treatment using a gas containing from about 3 to 100 mole percent water vapor, e.g. in nitrogen, at a temperature ranging from about 500° to 1000° C. Two hours of hydrothermal treatment has been shown to be effective.

5 Claims, No Drawings

CATALYSTS FOR PRODUCTION OF PHENOL AND ITS DERIVATIVES

This is a divisional of application Ser. No. 08/419,361 filed on Apr. 10, 1995 now abandoned.

Disclosed herein are improved catalysts for the production of phenol and its derivatives by single-step oxidative hydroxylation of benzene or other aromatic compounds by nitrous oxide and methods of making such catalysts.

BACKGROUND

The production of phenol by partial oxidation of benzene using nitrous oxide over a variety of catalysts ranging from vanadium pentoxide on silica to zeolites, e.g. ZSM-5 and ZSM-11 zeolite catalysts, at elevated temperatures, e.g. 300° to 450° C., has been disclosed. When benzene is replaced by a benzene derivative such a chlorobenzene, fluorobenzene, toluene or ethylbenzene, the corresponding substituted phenol can be produced. When phenol itself is the substituted benzene, the reaction products include dihydroxybenzenes such as hydroquinone, resorcinol and catechol. Phenol and its derivatives, for example, dihydric phenols, chlorophenols, nitrophenols, cresols and other hydroxyl-containing aromatic compounds are valuable products that find wide applications in industry. The most common commodity chemical of this class is phenol, which is used mainly in production of phenolic resins, caprolactam, nitrophenols and chlorophenols, etc. For decades, the researchers have searched for simple and efficient methods of syntheses of phenol and its derivatives. Iwamoto et al. in *J. Physical Chemistry* (ACS), Vol. 87, No. 6, (1983) p. 903–905 reported that single-step hydroxylation of aromatic compounds could be effected using nitrous oxide as an oxidant in the presence of traditional catalysts for partial oxidation, e.g. supported oxides of vanadium, molybdenum and tungsten. Iwamoto conducted the reaction at 550° C. with benzene conversion of 10% and selectivity towards phenol of 72%. Though these results were far superior to all previous achievements, still they turned out to be insufficient for practical use of the process, which dictated the need for search of more efficient systems.

The use of new type of catalysts, e.g. high silica aluminosilocates with zeolite structure, for the hydroxylation of benzene was reported by Suzuki et al. in the Chemical Society of Japan's *Chemistry Letters*, (1988) p. 953–956; by Gubelmann et al. in U.S. Pat. No. 5,055,623; and by Kharitonov et al. in U.S. Pat. No. 5,110,995. In the presence of such zeolite catalysts the hydroxylation of benzene and other aromatic compounds occurs at 300°–400° C. with selectivity towards phenol of 90–100%. However, catalyst activity remains sufficiently inadequate for commercial practice of this technology.

Researchers continue to discover new ways to improve the process parameters and/or enhance the efficiency of zeolites, e.g. by introducing various kinds of catalyst pretreatment. In this regard, Zholobenko reported in *Mendeleev Commun.*, (1993) No. 1, p. 28–29, a method for phenol production using zeolite catalyst that had been activated by high-temperature calcination in air. A drawback of this Zholobenko's method is that it does not provide any increase in catalyst activity at calcination temperatures below 700° C. More particularly, because the activation effect is significant at higher temperatures (750° C. and higher), Zholobenko's method is difficult to practically implement.

SUMMARY OF THE INVENTION

This invention solves several problems associated with insufficient performance and efficiency of zeolite catalysts in the nitrous oxide hydroxylation of benzene and its derivatives in the production of phenol and its derivatives. These problems are surprisingly solved by the use of a zeolite catalyst that is activated by simple and efficient method, e.g. exposure to water vapor at elevated temperature.

DETAILED DESCRIPTION OF PREFERRED EMBODIMENTS

This invention provides an improved zeolite catalyst for the production of phenol and its derivatives by oxidative hydroxylation of the corresponding aromatic compounds using nitrous oxide. The catalytic performance properties of such zeolite catalysts are enhanced using methods of this invention by treated the zeolite catalyst with a vapor-containing gas phase at a temperature in the range of 350° to 950° C. The amount of water vapor in the gas phase is not critical and can range from a low level of water vapor in a diluent gas to essentially pure water vapor. For instance, the gas phase can range comprise as low as 3 mole percent (mol %) water vapor in air or preferably in a substantially inert diluent gas phase comprising nitrogen, argon, helium, carbon dioxide and the like or mixtures thereof. The gas phase should, of course be essentially devoid of components that tend to poison catalysts. The gas phase can preferably comprise higher amounts of water vapor, e.g. 10 mol % or more, up to 100 mol %. The duration of the high temperature exposure of the catalyst to water vapor can vary depending on the desired enhancement and can readily be determined by routine experimentation.

Zeolites amenable to enhancement by the method of this invention include ZSM-5 and ZSM-11 zeolites which preferably are in the acid form and contain iron. Such zeolites are well-known in the art, are used for a variety of commercial processes and can be readily obtained from catalyst vendors, such as UOP, Mobil and others. Commercial zeolite catalysts are typically provided in a porous matrix of alumina or silica to provide in a durable pellet form that resists attrition in packed or fluid bed reactors. It has been discovered that the method of this invention can be advantageously applied to powdered or pelletized zeolite.

The enhanced performance zeolite catalysts prepared by the method of this invention are especially useful in the oxidation of aromatic compounds like benzene and benzene derivatives, e.g. chlorobenzene, fluorobenzene, toluene, ethylbenzene and the like including phenol. Such oxidation is effected by passing a feed gas mixture of the phenol, nitrous oxide and, optionally, diluent gas such as nitrogen, argon, carbon dioxide and the like, to a zeolite catalyst bed at a temperature in the range of 225° to 450° C. or higher, e.g. above 500° C. Process conditions, including feed composition, reaction temperature, flow rates and the like can be varied by those skilled in the art depending on the desired process parameters, e.g. selectivity of phenol production, conversion of nitrous oxide, phenol concentration in the product gas, catalyst productivity and the like. For instance, the molar ratio of nitrous oxide to benzene in the feed gas mixture can range from 100:1 to 1:100. In certain preferred embodiments, there are advantages to operating the process with a molar excess of the aromatic compound.

In one aspect of this invention the zeolite catalysts that have been hydrothermally treated are characterized by stable performance in a desired catalytic conversion, i.e. low reduction of benzene conversion in the production of phenol by oxidation of benzene with nitrous oxide at 350° C. Preferred catalysts of this invention, e.g. ZSM-5 or ZSM-11 zeolite catalysts, will exhibit a ratio of benzene conversion after 3 hours of continuous operation to initial benzene conversion is at least 40%. In more preferred catalysts the ratio will be at least 50%. The following examples illustrate catalysts where such ratio is about 70%.

The catalysts of this invention having been hydrothermally treated can be identified by a resistance to hydrothermal treatment. For instance, an iron-containing, acidified, zeolite catalyst of this invention can be characterized in that hydrothermal treatment of such a catalyst for two hours with a gas consisting of 50 mole percent air and 50 mole percent water and at a temperature of 600° C. does not increase by more than 10% the benzene conversion performance of the catalyst when used in the catalytic hydroxylation of benzene to phenol in a gas stream consisting of 75 mole percent helium, 5 mole percent benzene and 20 mole percent nitrous oxide at 350° C.

The advantages of this invention are illustrated by the following examples where the enhanced performance of the zeolites are demonstrated by the oxidation of benzene using nitrous oxide.

EXAMPLE 1

An $SiO_2$-based zeolite catalyst containing $4.3\times10^{-4}$ moles of $Fe_2O_3$ and $2.3\times10^{-2}$ moles of $Al_2O_3$ per mole $SiO_2$ was prepared according to the methods disclosed by Kharitonov in U.S. Pat. No. 5,110,995. After the organic template material was burned off, the zeolite was treated with acid to transform it into the H-form and calcined in a flow of dry air at 550° C. for two hours. For catalytic property testing a tubular reactor was prepared by loading about 2 cc of a 0.5–1.0 mm fraction of the zeolite into a quartz tube having a 0.7 cm internal diameter. The zeolite-filled tubular reactor was heated to 350° C. and fed with a reaction gas mixture comprising 5 mol % benzene and 20 mol % nitrous oxide in helium. The product gas flowing from the reactor was periodically analyzed by gas chromatography. The gas analysis data was used to calculate benzene conversion (X) and selectivity towards phenol (S), which are reported in Table 1. It was observed that the catalyst was apparently being deactivated during the run because of coke deposition. 20 minutes after the start of feed gas flow to the reactor, measurements were taken to determine an initial benzene conversion, $X_o$, of 8.5% and an initial selectivity, $S_o$, of 92.5%. After 3 hours of continuous operation, the benzene conversion was determined to be 3.0%, indicating a decline in catalyst activity. The ratio of benzene conversion to initial benzene conversion ($X/X_o$) of 35% characterizes the catalyst stability in operation. No decrease in selectivity was observed during any of the runs.

EXAMPLE 2

Catalyst prepared substantially in the manner of Example 1 was additionally subjected to hydrothermal treatment for two hours by exposure to air containing 50 mol % water at 500° C. for two hours in the presence of air containing 50 mol % water. Catalytic properties of the hydrothermally treated catalyst reported in Table 1 shows a substantial increase in initial benzene conversion to 18.5%.

EXAMPLES 3–8

These examples illustrate aspects of the invention where the hydrothermal treatment temperature is varied. In these examples catalyst samples were prepared essentially in the manner of Example 2 except that hydrothermal treatment was carried out at 550°–1000° C. The observed catalytic properties reported in Table 1 show that an optimum hydrothermal treatment temperature can be readily determined by routine experimentation to provide a catalyst with desired initial or long term conversion characteristics. More surprisingly, as benzene conversion increases with hydrothermal treatment, e.g. from 8.5% to 37%, catalyst stability is also increased by a factor of 2, e.g. $X/X_o$ is increased from 35% to 70%. Such treatment at very high temperature, e.g. around 1000° C., is not advisable because it apparently leads to activity decrease.

TABLE 1

| Example | Treatment temp. °C. | Initial Catalytic Properties | | Activity after 3 hours on-stream | |
|---|---|---|---|---|---|
| | | $X_o(\%)$ | $S_o(\%)$ | $X(\%)$ | $X/X_o(\%)$ |
| 1 | no treatment | 8.5 | 92.5 | 3.0 | 35 |
| 2 | 500 | 18.5 | 93.5 | 4.5 | 24 |
| 3 | 550 | 33.5 | 93.0 | 12.0 | 34 |
| 4 | 600 | 37.0 | 95.0 | 15.5 | 42 |
| 5 | 650 | 36.5 | 93.5 | 18.0 | 49 |
| 6 | 700 | 31.5 | 95.5 | 22.0 | 70 |
| 7 | 750 | 27.5 | 96.0 | 18.5 | 67 |
| 8 | 1000 | 5.5 | 95.0 | 2.7 | 49 |

EXAMPLES 9–12

This example illustrates aspects of this invention where the water content of the hydrothermal treatment gas varied. In these examples catalyst samples were prepared essentially in the manner of Example 2 except that hydrothermal treatment was carried out with a treatment gas at 600° C. and containing from 2.5 to 100 mol % water vapor. The catalytic data reported in Table 2 shows that increasing the concentration of water vapor in the hydrothermal treatment gas can provide a catalyst with substantially increased process efficiency. For instance, benzene conversion increased from 8.6% to 38.5% with simultaneous increase in stability and some increase in selectivity.

In Example 9 hydrothermal treatment was carried out under conditions potentially similar to calcination of the catalyst in air, e.g. at 2.5 mol % water vapor. Comparison of Examples 9 and 1 shows that such concentration of water is not sufficient for noticeable activation of the catalyst.

TABLE 2

| Example | $C_{H2O}$ (mol. %) | Initial Catalytic Properties | | Activity after 3 hours on-stream | |
|---|---|---|---|---|---|
| | | $X_o(\%)$ | $S_o(\%)$ | $X(\%)$ | $X/X_o(\%)$ |
| 9 | 2.5 | 8.6 | 92.5 | 3.0 | 35 |
| 10 | 10 | 15.5 | 93.0 | 5.0 | 33 |
| 11 | 50 | 35.0 | 94.0 | 15.5 | 45 |
| 12 | 100 | 38.5 | 95.0 | 19.0 | 50 |

EXAMPLES 14–16

These examples illustrate the beneficial effect of the process of this invention on a variety of catalysts useful in the hydroxylation of benzene using nitrous oxide to produce phenol. Zeolites with a composition reported in Table 3 were all evaluated to determine an initial benzene conversion and phenol selectivity. The zeolites were then hydrothermally treated by exposure for two hours to a 500° C. gas containing 50 mol % water. It can be seen that such hydrothermal treatment substantially enhances the process characteristics of such varied zeolite compositions.

TABLE 3

| Example | Chemical Composition | Catalytic Properties | | | |
|---|---|---|---|---|---|
| | | Before treatment | | After treatment | |
| | | $X_o(\%)$ | $S_o(\%)$ | $X_o(\%)$ | $S_o(\%)$ |
| 14 | $1.1 \times 10^{-2}$ of $Al_2O_3SiO_2$ | 8.0 | 97.0 | 30.0 | 98.0 |
| 15 | $3.4 \times 10^{-3}$ of $Fe_2O_3$ $8.6 \times 10^{-3}$ $Al_2O_3SiO_2$ | 21.5 | 83.5 | 46.5 | 87.5 |
| 16 | $5.7 \times 10^{-3}$ of $Fe_2O_3SiO_2$ | 15.0 | 91.0 | 31.5 | 90.0 |

These examples show the essence of the proposed invention, but are in no way exclusive, meaning that optimal conditions of hydrothermal activation (temperature, time, water vapor concentration, etc.) can be different for different types of catalysts and reactions intended for the use of the catalyst. In particular, high efficiency of the activated catalysts enables to carry the process not only in excess of nitrous oxide, but also in excess of the aromatic species, e.g. up to molar ration of aromatic species to nitrous oxide of 100:1. The advantage of performing the process in excess of the aromatic compound is that under such conditions complete nitrous oxide conversion is achieved. This leads to significant technology simplification because in this case there is no need to isolate unreacted nitrous oxide and return it into the reaction.

While specific embodiments have been described herein, it should be apparent to those skilled in the art that various modifications thereof can be made without departing from the true spirit and scope of the invention. Accordingly, it is intended that the following claims cover all such modifications within the full inventive concept.

What is claimed is:

1. A method for the catalytic production of phenol or derivative thereof comprising reacting benzene or derivative thereof with nitrous oxide in the presence of a zeolite catalyst wherein, prior to said reaction, the catalyst performance has been enhanced by hydrothermal treatment with a gas comprising 3 to 100 mole percent water at a temperature of 350° to 950° C.

2. A method according to claim 1 wherein said zeolite catalyst is a ZSM-5 or ZSM-11 zeolite catalyst.

3. A method according to claim 2 wherein said catalyst is an acidified, iron-containing aluminosilicate zeolite.

4. A method according to claim 3 wherein said gas comprises at least 10 mole percent water.

5. A method according to claim 4 wherein said gas is at a temperature of at least 500° C.

* * * * *